United States Patent [19]

Nishino et al.

[11] Patent Number: 5,773,273
[45] Date of Patent: Jun. 30, 1998

[54] GERANYLGERANYL DIPHOSPHATE SYNTHASE AND DNA CODING THEREFOR

[75] Inventors: Tokuzo Nishino; Shinichi Ohnuma; Manabu Suzuki, all of Sendai; Chikara Ohto, Toyota; Chika Asada, Toyota; Yuka Higuchi, Toyota; Yoshie Takeuchi, Toyota, all of Japan

[73] Assignee: Toyota Jidosha Kabushiki Kaisha, Toyota, Japan

[21] Appl. No.: 410,167

[22] Filed: Mar. 24, 1995

[30] Foreign Application Priority Data

Mar. 24, 1994 [JP] Japan .................................... 6-053804
Nov. 25, 1994 [JP] Japan .................................... 6-315572

[51] Int. Cl.[6] .............................. C12N 9/10; C12N 15/54; C12N 15/70; C12P 7/04
[52] U.S. Cl. ......................... 435/193; 435/69.1; 435/69.7; 435/131; 435/252.3; 435/252.33; 435/320.1; 536/23.2; 536/23.4
[58] Field of Search ..................................... 435/69.1, 131, 435/193, 252.3, 320.1, 69.7, 252.33; 536/23.2, 23.4

[56] References Cited

U.S. PATENT DOCUMENTS 4,652,639   3/1987   Stabinsky ............................. 345/91.52

FOREIGN PATENT DOCUMENTS 674000      9/1995   European Pat. Off. .
WO91/13078  9/1991   WIPO .

OTHER PUBLICATIONS

Fortkamp, E., et al., DNA, vol. 5, Cloning and expression in *Escherichia coli* of a synthetic DNA for hirudin, the blood coagulation inhibitor in the leech, pp. 511–517 1986.
Zhang, D., et al., Journal of Organic Chemistry, vol. 58, "Biosynthesis of archeabacterial lipids in*and Methanobacterium thermoautotrophicum* ", pp. 3919–3922. 1993.

Ammendola, S., et al., Biochemistry, vol. 31, "Thermostable NAD+–dependent alcohol dehydrogenase from*Sulfobacterium solfataricus*: Gene and protein sequence determination and relationship to other alcohol deydrogenases", pp. 12514–12523. 1992.

Chen, A., et al., Protein Science, vol. 3, "Isoprenyl diphosphate synthases: Protein sequence comparisons, a phylogenetic tree, and predictions of secondary structure", pp. 600–607. 1994.

Chen, A., & Poulter, C.D., Archives of Biochemistry and Biophysics, vol. 314, "Isolation and characterization of idsA: the gene for the short chain isoprenyl diphosphate synthase form *Methanobacterium thermoautotrophicum*", pp. 399–404. 1994.

Biochemistry, vol. 66, No. 7, p. 1036, abstract No. 4690 (1994), M. Watanabe et al.: *Phosphorylation of geranylgeraniol by cell–free extracts of highly thermophilic bacterium Sulfolobus acidocaldarius (with translation)* .

Biochemistry, vol. 65, No. 8, p. 893, Abstract No. 3098 (1993), Eiji Yamahara et al.: *Research on enzymes contributing to lipid biosynthesis by the highly thermophilic acidophilic bacterium Sulfolobus acidocaldarius* (with translation).

Plant Physiol. 104: 1469–1470 (1994), Pablo A. Scolnik et al.: *Nucleotide Sequence of an Arabidopsis cDNA for Geranylgeranyl Pyrophosphate Synthase* .

N. Misawa, et al., Journal of Bacteriology, vol. 172, No. 12, pp. 6704–6712 (1990).

(List continued on next page.)

*Primary Examiner*—Robert A. Wax
*Assistant Examiner*—William W. Moore
*Attorney, Agent, or Firm*—Kenyon & Kenyon

[57] ABSTRACT

DNA coding for thermostable geranylgeranyl diphosphate (GGDP) synthase derived from *Sulfolobus acidocaldarius* is provided. The DNA is useful for production of GGDP synthase, which is, in turn, useful for production of GGDP.

21 Claims, 7 Drawing Sheets

OTHER PUBLICATIONS

C.B. Michalowski, et al., The Journal of Biological Chemistry, vol. 266, No. 18, pp. 11866–11870 (1991).

M. Kuntz, et al., Plant Journal, vol. 2, No. 1, pp. 25–34 (1992).

A. Carattori, et al., The Journal of Biological Chemistry, vol. vol. 266, No. 9, pp. 5854–5859 (1991).

D. Taylor, et al., Journal of Bacteriology, vol. 154, No. 2, pp. 580–590 (1983).

F.L. Brinkhaus, et al., Archives of Biochemistry and Biophysics, vol. 266, No. 2, pp. 607–612 (1988).

A. Chen, et al., Journal of Biological Chemistry, vol. 268, No. 15, pp. 11002–11007 (1993).

A. Tachibana, et al., Biosci Biotech Biochem, vol. 57, No. 7, pp. 1129–1133 (1993).

S.Ohnuma, et al., Journal of Biological chemistry, vol. 269, No. 20, pp. 14792–14797 (1994).

GERANYLGERANYL DIPHOSPHATE SYNTHASE AND DNA CODING THEREFOR

BACKGROUND OF INVENTION

1. Field of the Invention

The present invention relates to DNA sequence for production of geranylgeranyl diphosphate synthase derived from *Sulfolobus acidocaldarius* and a transformant with said DNA as well as processes for production of the geranylgeranyl diphosphate synthase and of geranylgeranyl diphosphate using said enzyme.

2. Related Art

Geranylgeranyl diphosphate (GGDP) has four double bonds and includes eight geometrical isomers. GGDP is synthesized in vivo by condensation of isopentenyl diphosphate and farnesyl diphosphate, and is an important intermediate for biosynthesis of isoprenoids and isoprenoid-containing compounds such as calotenoids, diterpenes, vitamines etc. GGDP synthases are found in bacteria, plants, fungi and algae. A large amount of the native isomer of isoprenoids is expressed by introduction by genetic engineering technique of a gene for GGDP synthase into an appropriate host, and where GGDP synthase is provided in low cost, it can be used for the production of the native isomer of GGDP.

In such a point of view, researches of genes coding for bacterial GGDP synthase and manipulation thereof as well as the production of the synthase have been attempted, and so far only two bacterial genes derived from different sources are known (photosynthetic bacterium *Rhodopseudomonos capusulata* (J. Bacteriol. 154, p. 580–590, 1983; and a phytopathogenic bacterium *Erwinia uredovora* (J. Bacteriol., 172, p. 6704–6712, 1990). These GGDP synthases are unstable, and for example, an enzyme derived from *Erwinia uredovora* is rapidly inactivated at 55° C. (see, Table 3).

SUMMARY OF THE INVENTION

The unstable enzymes derived from that mesophiles are not sufficient for practical production of GGDP, and especially it is essential to produce a thermostable GGDP synthase. Accordingly, an object of the present invention is to provide primary structure of a gene coding for a thermostable GGDP synthase for developing a process of production of the thermostable GGDP synthase, and to modify microorganisms originally not producing GGDP (such as *E. coli*) to produce GGDP.

To achieve the above object, we found a GGDP synthase expressed from DNA fragment of *Sulfolobus acidocaldarius* which is known as an extreme thermophile and acidophilic archaebacterium bacterium. We succeeded to express the GGDP synthase using genetic engineering technique.

The present invention provides a DNA coding for GGDP synthase derived from *Sulfolobus acidocaldarius*, a recombinant vector having said DNA, as well as recombinant microbial cells to which said gene is introduced by said vector, and the use thereof for the production of GGDP synthase or GGDP per se.

DETAILED DESCRIPTION

According to the present invention, DNA coding for GGDP synthase includes any DNA unit which, on the expression thereof, provide protein having GGDP synthase activity. One particular DNA is that coding for the amino acid sequence shown in SEQ ID NO: 1. The present DNA further include a DNA coding for said amino acid sequence and an additional amino acid sequence (for example, as a fusion protein). A particular example of such a DNA is that having the nucleotide sequence shown in SEQ ID NO: 1.

One embodiment of the present gene is that coding for an amino acid sequence starting with the first Met and ending at 330th Lys in SEQ ID NO: 1. However, there is a case where the first Met is removed by post-translational processing, or the desired enzyme is produced as a fusion protein comprising another peptide. In these cases, the codon coding for the first Met is not present. According to an embodiment of the present invention, the present gene encodes a protein comprising an amino acid sequence starting with the second Ser and ending at the 330th Lys in SEQ ID NO: 1.

An embodiment of the present gene comprises a nucleotide sequence starting with the first nucleotide "A" and ending at 990th nucleotide "A".

It is generally known that same enzymes which are derived from the same species or the same genus involving minor difference in their amino acid sequences by a natural or antificial mutation such as substitution, addition and/or deletion of one or more nucleotides.

According to the invention described in the present specification, it is possible to clone a gene encoding the same enzyme having a difference in amino acid sequence shown in SEQ ID NO: 1. Amino acid sequence drived from such a gene may have a very high homology with the amino acid sequence shown in SEQ ID NO: 1, for example, homology of at least 90%, and further at least 98%. Accordingly, the present invention includes not only a gene coding for GGDP synthase having the amino acid sequence shown in SEQ ID NO: 1, but also gene encoding a protein having a GGDP synthase activity and an amino acid sequence with at least 95% homology, for example 98% homology to that shown in SEQ ID NO: 1.

It is well known for an enzyme that in portions other than portions which is necessary for a function, particular amino acid residues are not essential. Modifications such as substitution, deletion and/or addition of one or a few amino acids can be carried out maintaining the enzyme activity in such non-essential regions. Using general technique such as site-directed mutagenesis with a probe having antificial sequence, we can modify up to 20 amino acids, for example up to 10 amino acids. Substitution, deletion and/or addition of an amino acid sequence can be done using restriction enzymes and/or joining enzymes, ligases.

The present invention includes a gene which encodes a protein having GGDP synthase activity and including an amino acid sequence shown in SEQ ID NO: 1 can be modified by substitution, deletion and/or addition of up to 20 amino acids, for example, up to 10 amino acids.

DNA fragment of the present invention can be prepared according to a procedure per se known as described in detail hereinafter from *Sufolobus acidocaldarius* available from institutes storing various microorganism, in a form of various length of DNA according to the purpose for using the DNA.

Namely, the present DNA can be prepared by extracting the genomic DNA from *Sulfolobus acidocaldarius*, cleaving the extracted DNA with, for example, one or more appropriate restriction enzymes to form fragments, inserting the fragments to vectors to prepare a genomic library, and selecting a vector comprising a DNA coding for a desired enzyme by detection of the expression of the desired enzyme. A definite procedure is described in Example 1. a) to d).

Since the present invention discloses a particular nucleotide sequence encoding GGDP synthase, DNA comprising said nucleotide sequence or a nucleotide sequence modified therefrom can be prepared by chemical synthesis. This DNA fragment or a part thereof can be used as primer to synthesize a modified DNA encoding a protein having GGDP synthase activity according to a conventional procedure such as site-directed mutagenesis or PCR method.

The present invention provides recombinant vectors comprising the above-mentioned DNA fragment of the present invention. The recombinant vector can contain a region having functions to express the GGDP synthase gene.

It is known that there are two regulation steps of the gene expression, transcription and translation. Conventional host cell of *E. coli* has also these regulation systems. As promoter sequences controlling the transcription initiation of mRNA, wild type sequences (for example, lac, trp, bla, lpp, PL, PR, tet, T3, T7 etc.) as well as mutant thereof (for example lacUV5) and artificial fusion sequences of promoter sequences (for example, tac, trc etc.) are known, and can be used in the present invention. The distance between the riposome-binding site (GAGG or similar sequence) and the initiation codon ATG or GTG in some cases are important as a factor which regulates translation of a protein from mRNA. It is well known also that a terminator structure which can stop transcription effects on the efficiency of a recombinant protein expression (for example, a vector containing rrnBT1T2 is commercially available from Pharmacia).

Vectors which can be used for construction of the present recombinant vectors include commercially available vectors per se, and vectors modified according to purposes. For example, pBR322, pBR327, pKK223-3, pKK233-2, pTrc99 etc. having a replicon derived from pMB1; pUC18, pUC19, pUC118, pUC119, pHSG298, pHSG396, which have been modified to increase the copy number; pACYC177, pACYC184 etc. having a replicon derived from p15A; as well as plasmids derived from pSC101, ColE1, R1, F-factor etc. are mentioned.

Moreover, in addition to plasmids, viral vectors such as λ phage, M13 phage etc., and transpson can be used for introduction of a gene into a host. These vectors are described in Molecular Cloning (J. Sambrook, E. F. Fritsch, T. Maniatis; Cold Spring Harbor Laboratory Press); Cloning Vector (P. H. Pouwels, B. E. Enger.Valk, W. J. Brammer; Elsevier); and various catalogues attached to commercial products.

We can introduce a DNA fragment coding for GGDP synthase and, if necessary, a DNA fragment which can control expression of said enzyme gene into a vector according to known methods using appropriate restriction enzymes and ligases, as described in detail hereinafter. Plasmids PGGPS1 and pMa1GG1 are representative examples of the present plasmids thus constructed.

Microorganisms to be transformed with a recombinant vector thus obtained include *Escherichia coli* or microorganisms belonging to the genus Bacillus. $CaCl_2$ method, protoplast method etc., as described in, for example, Molecular Cloning (J. Sambrook, E. F. Fritsch, T. Maniatis; Cold Spring Harbor Laboratory Press), DNA Cloning Vol. I to III (D. M. Glover; IRL PRESS) etc. can be used for transformation.

A typical transformant of the present invention can be obtained as pGGPS1/DH5α.

We described methods for expression of the desired gene in *E. coli* above in detail, according to the present invention. A DNA coding for a GGDP synthase can be introduced into other conventional expression vectors according to conventional procedures, such as other prokaryotic cells, lower eukaryotic cells including unicellular host such as yeast, or higher eukaryotic cells such as silk-worm cells. These transformed host cells can be cultured to produce GGDP synthase enzyme.

These transformants or recombinant microbial cells can accumulate GGDP synthase in the cells or in the culture medium while culturing in a medium suitable for said cells such as *E. coli*. We can prepare GGDP synthase from the cells as follow; lysing the cells with physical disraption or by treatment with a cell-lysing enzyme, removing cell debris to prepare a cell-free extract containing the enzyme, and then isolating and purifying GGDP synthase. We recommend lysozyme as cell-lysing enzyme and sonication as physical disraption. Most of proteins derived from *E. coli* is denatured by heating at 55° C. The enzyme can be isolated and purified by various chromatographies including gel filtration chromatography, ion exchange chromatography, hydrophobic reversed chromatography, and ultrafiltration and the like alone or in combination. Reducing reagent such as β-mercaptoethanol, dithiothreitol et al., protecting agent against proteases such as PMSF, BSA etc., or metal ions such as magnesium ion can be used to stabilize the desired enzyme during isolation and purification processes, as an enzyme stabilizer.

Activity of GGDP synthase can be determined by, for example, a method described in Example 1. e) It is recommended to isolate and purify GGDP synthase while checking enzyme activity.

The present invention further provides a process for production of GGDP. We can make a host transformed with a DNA encoding GGDP synthase contain DNAs coding for other enzymes in a GGDP biosynthesis pathway. This recombinant can synthesize GGDP by calturing, which can be then prepared and purified.

According to the present invention, the above-mentioned transformant is cultured to produce GGDP synthase, and the isolated enzyme or enzyme-containing product such as partially purified enzyme sample, enzyme-containing cells etc. can be used with substrates, i.e., isopentenyl diphosphate, dimethylallyl diphosphate, geranyl diphosphate or farnesyl diphosphate to synthesize GGDP, which is then recovered.

EXAMPLES

We show primary structure of nucleotide sequence, plasmids and transformants in the following part as well as GGDP synthase and GGDP of the present invention. The present invention is not limited within these Examples.

Example 1

We carried out procedures with reference to, mainly, the above-cited Molecular Cloning, and DNA Cloning as well as catalogues from Takara Shuzo. Most of enzymes were purchased from Takara Shuzo. Reversed phase thin layer chromatography (TLC) plates LKC-18 were purchased from Whatman, Kieselgel 60 thin-layer chromatography (TLC) plates LKC-18 were purchased from Merck. *Sulfolobus acidocaldarius* ATCC 33909 used in the present invention is registered in and available without any limitation from America Type Culture Collection (ATCC).

a) Preparation of chromosomal DNA from *Sulfolobus acidocaldarius*

Cells of ATCC 33909 strain were cultured in the 1723 medium described in ATCC catalogue. Genomic DNA was prepared from the cultured cells, according to Current Protocols in Molecular Biology published by Wiley Interscience.

b) Preparation of a genomic DNA library of *Sulfolobus acidocaldarius*

The chromosomal DNA was partially digested with a restriction enzyme Sau3AI, and subjected to 0.5% agarose gel electrophoresis. A block of the agarose gel containing DNA fragments of 3 kbp to 6 kbp was fractionated, and DNA was extracted therefrom. 2.7 µg of this size-fractionated DNA and 1.4 µg of pUC119 plasmid DNA cleaved with BamHI and dephosphorylated were ligated using DNA ligase. The ligation cocktail was used to transform *E. coli* DH5α. The transformants were then stored at −70° C. The library thus constructed was screened.

c) Preparation of competent cells carrying plasmid pACYC-IB A 2.8 kbp of SnaBI-HpaI DNA fragment containing crtI (phytoene synthase gene) and crtB (phytoene desaturase gene) of *Erwinia uredovora* was prepared from pCAR25 (N. Misawa et al., J. Bacteriol. 172. 6704–6712 (1990)). *Erwinia uredovora* is available from ATCC19321. It is easily grown with LB medium. That 2.8 kbp DNA fragment can be cloned, for instance, using popular techniques of Southern analysis or PCR with probe DNAs synthesized from crtI or crtB nucleotide sequences retrievable from GenBank accession No. D90087.

This DNA fragment was ligaled with an EcoRI linkers and cleaved with a restriction enzyme EcoRI, and joined using DNA ligase to a plasmid pACYC184 which had been digested with EcoRI and dephosphorylated. The ligation cocktail was then used to transform *E. coli* pACYC-IB/ pH5α. Competent cells were prepared by CaCl₂ method.

d) Selection of GGDP synthase gene

Plasmid DNAs were purified from *E. coli* containing *Sulfolobus acidocaldarius* genomic DNA library constructed in the above-mentioned procedure b) according to an alkaline method, and 10 nanograms of the DNA was used to transform the *E. coli* carrying the crtI and crtB genes prepared by the above-mentioned method c). The transformants were cultured on an LB agar plates containing 50 µg/ml tetracycline and 50 µg/ml ampicillin.

10 positive red colonies were obtained by visually selecting among about 4,000 transformants. Among these 10 colonies a plasmid named pGGPS1 was isolated from one colony. A 2.3 kbp of HindIII fragment in pGGPS1 insert DNA was subcloned into pUC118. This subclone DNA was then introduced into *E. coli* cells carrying the crtI and crtB gene. This clone produced red colonies. Since the presence of GGDP synthase gene in the HindIII fragment was demonstrated, nucleotide sequence of this 2.3 kbp was determined by dideoxy chain termination method.

Figure 1:
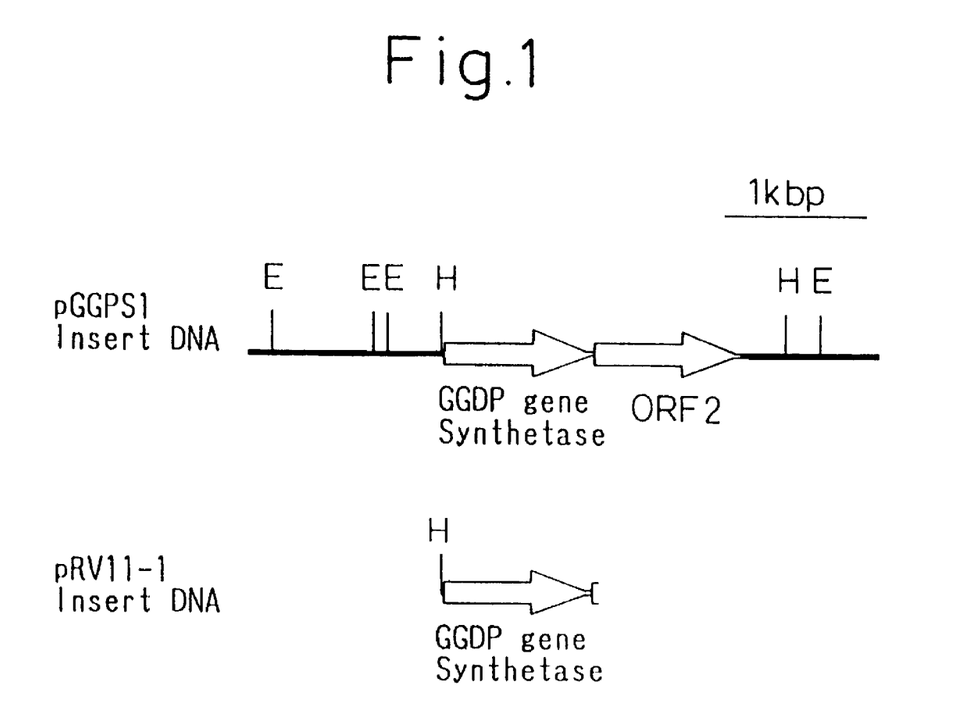
FIG. 1 represents an insert DNA fragment and a restriction enzyme map thereof in plasmids pGGPS1 and pRV11-1 containing the present DNA sequence. "E" and "H" represent EcoRI and HindIII recognition sites respectively.

As a result, the 2.3 kbp fragment included two open reading frames (ORF-1 and ORF-2) as shown in FIG. 1.

Accordingly, a plasmid pRV11-1 lacking the downstream ORF-2 was constructed, and enzyme activity of an expression product was determined according to the method e).

e) Assay of GGDP synthase activity

The plasmid pRV11-1 obtained in the above-mentioned method d) was used to transform *E. coli* DH5α, which was then cultured in 100 ml of LB medium containing 50 µg/ml ampicillin at 37° C. overnight. The cells were harvested and disrupted by sonication in 8 ml of Sonic buffer (10 mM 2-mercaptoethanol, 1 mM EDTA, 50 mM Tris-HCl (pH7)), and the homogenate was heated at 55° C. for 60 minutes and centrifuged at 10,000×g for 10 minutes. The supernatant was used to assay for GGDP synthase activity.

The assay mixture contained, in a final volume of 1 ml, 0.48 µmol of [1–$^{14}$C] isopentenyl diphosphate (1.92 GBq/mmol), 25 µmol of (all-E) farnesyl diphosphate, 5 µmol of MgCl₂, 25 µmol of Tris-HCl (pH6.8) and 0.3 mg the above crude enzyme. This mixture was incubated at 550° C. for 30 minutes, and chilled in an ice bath to stop the reaction. The reaction mixture was extracted with 3 ml of 1-butanol saturated with water, and the radioactivity in the 1-butanol layer was counted to determine GGDP synthase activity. A result is shown in Table 1. It was shown that all of the clones thus obtained have a gene which was expected to encode a thermostable GGDP synthase. In addition, an assay of an extract from the clone containing pRV11-1 showed that the ORF-1 is GGDP synthase gene.

TABLE 1

Result of assay for GGDP synthase activity derived from plasmid of the present invention (Radioactivity of 1-butanol extract is shown in dpm unit.)

| Cell-free extract from: | Enzyme activity (dpm) |
|---|---|
| *E. coli* DH5α (no heat treatment) | 3,310 |
| *E. coli* DH5α (heat treatment) | 0 |
| *E. coli* DH5α/pGGPS1 (heat treatment) | 11,900 |
| *E. coli* DH5α/pRV11-1 (heat treatment) | 8,770 | f) Analysis of GGDP synthase product

Identification of a product produced by the heat-denatured cell-free extract was carried out.

Figure 2A:
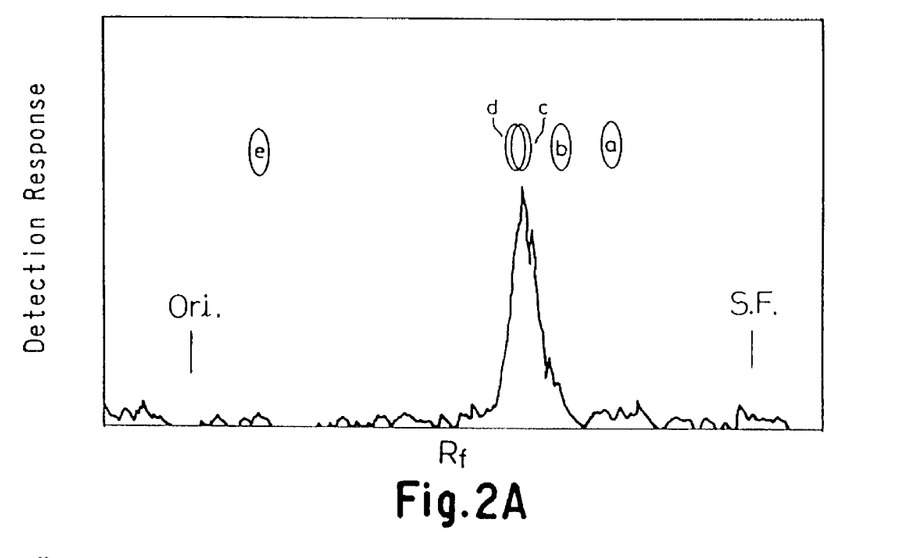
FIG. 2 represents a result of analysis of products of a reaction catalyzed by product from plasmid containing DNA of the present invention. Panel A represents a result of thin layer chromatography using LKC-18, and panel C represents a result of that using Kiselgel 60 TLC. Panel B is for a control sample analysed by LKC-18. Circles a, b, c, d and e correspond to geraniol, (all-E) farnesol, (all-E) geranylgeraniol, (2Z, 6E, 10E) geranylgeraniol and (all-E) decaprenol respectively.
Figure 2B:
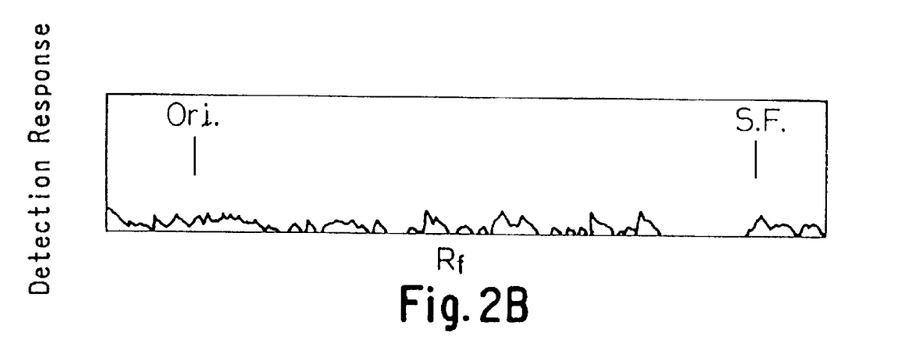
Figure 2C:
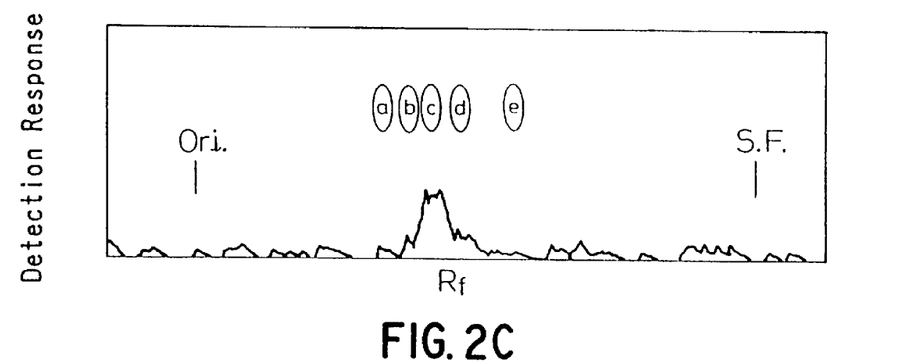

The products obtained from the incubation of [1–$^{14}$C] isopentenyl diphosphate and furnesyl diphosphate with a cell-free extract from selected positive transformant were hydrolyzed with an acid phosphatase according to a method of Fujii et al. (Fujii et al., (1982) Biochim. Biophys. Acta 712, p. 716–718). The hydrolyzed alcohols were extracted with pentane. The pentane-soluble products were analyzed by reversed phase LKC-18 thin layer chromatography using a mixed solvent of acetone/water (9:1) and normal phase Kieselgel 60 thin layer chromatography using a mixed solvent of benzene/ethyl acetate (9:1). A result is shown in FIG. 2. It is clearly shown that the radio-active alcohol derived from the recombinant product is (all-E) geranylgeraniol which is a derivative from (all-E)-GGDP.

Accordingly, successful cloning of GGDP synthase gene from *Sulfolobus acidocaldarius* was confirmed.

g) Partial purification of GGDP synthase derived from cloned gene

A heat-treated cell-free extract from a cell lysate of recombinant *E. coli* carrying a GGDP synthase gene was precipitated with 30–60% saturation of $(NH_4)_2SO_4$. The precipitated protein fraction was dialyzed and chromatographed on a DEAE Toyopearl 650M column (1.0×16 cm) equilibrated with buffer A (1 mM EDTA, 10 mM Tris-HCl (ph7.7)); Elution was performed with a linear gradient from 0 to 0.85M NaCl in buffer A. Fractions containing GGDP synthase were collected and dialyzed against buffer A. The dialysate was applied to a Mono Q column (5×50 mm) equilibrated with buffer A; Elution was performed with a linear gradient of 0–0.85M of NaCl in buffer A. A fraction containing GGDP synthase was analysed by 10% SDS polyacrylamide gel electrophoresis and the gel was stained with Coamassie Briliant Blue.

After these operations, a specific activity reached 8.7 nmol/min./mg protein.

h) Substrate specificity of GGDP synthase derived from cloned gene

Substrate specificity of GGDP synthase derived from the cloned gene was tested using allyl diphosphate substrates shown in Table 2. As a result, it was found that dimethylallyl diphosphate, geranyl diphosphate and (all-E) farnesyl diphosphate can be substrates.

TABLE 2

Substrate specificity of GGDP synthase derived from cloned gene of the present invention

| Substrate | Enzyme activity (dpm) |
| --- | --- |
| Dimethylallyl diphosphate | 24,900 |
| Geranyl diphosphate | 20,900 |
| (all-E) Farnesyl diphosphate | 15,300 |
| (2Z, 6E) Farnesyl diphosphate | 260 |
| (all-E) Geranylgeranyl diphosphate | 0 |
| (2Z, 6E, 10E) Geranylgeranyl diphosphate | 50 | i) Thermostability of GGDP synthase derived from cloned gene

Figure 3:
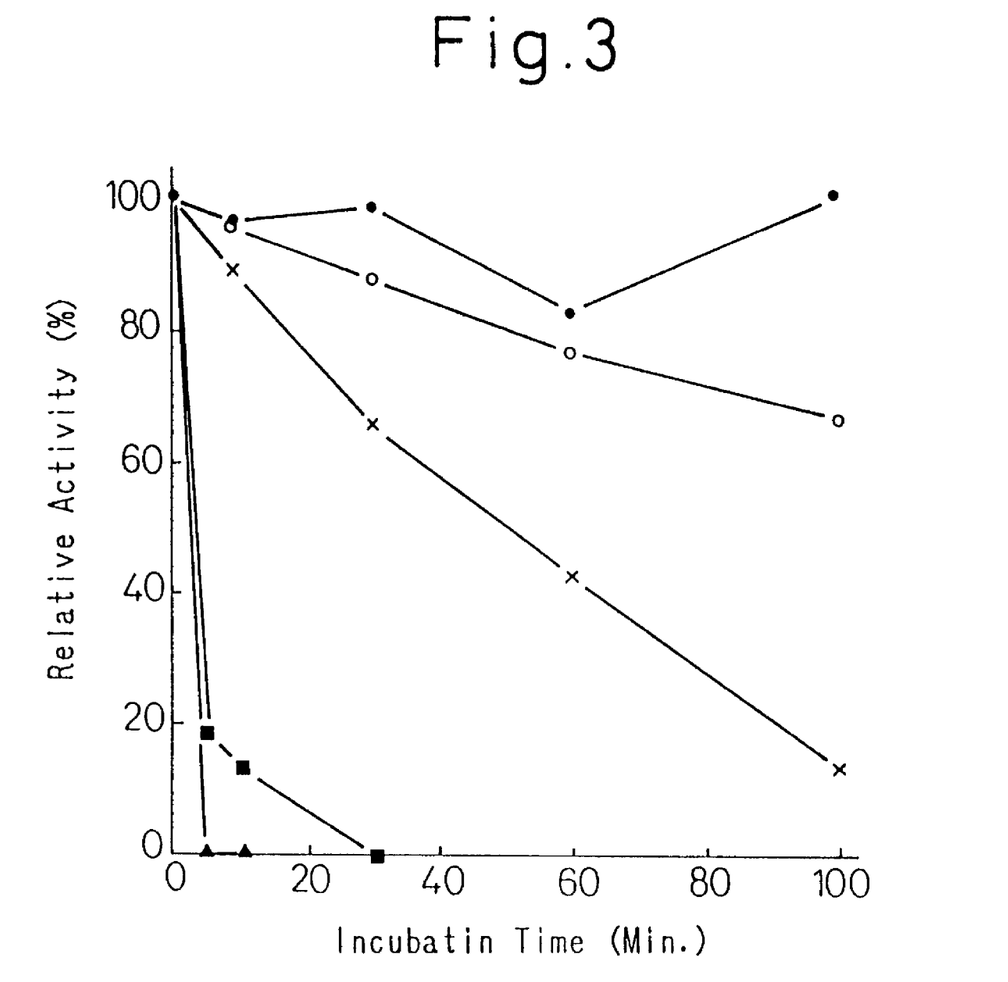
FIG. 3 represents thermostability of the present GGDP synthase by determining the remaining enzyme activities. The symbols, solid circle, white circle, cross, solid square, and solid triangle show result of treatment at 60° C., 70° C., 80° C., 90° C. and 100° C. respectively.

The GGDP synthase derived from the gene cloned from *Sulfolobus acidocaldarius* was heat-treated and remaining activity was determined. After heating at 60° C. for 100 minutes, at least 95% of activity was maintained. A result is shown in FIG. 3.

For comparison, thermostability of GGDP synthase derived from *Erwinia uredovora* (product of crtE) was as follow.

TABLE 3

Thermostability of GGDP synthase derived from *Erwinia uredovora* (crtE product)

| Combination of treatment | Remaining activity |
| --- | --- |
| 55° C. 5 min. | 55% |
| 55° C. 10 min. | 47% |
| 55° C. 30 min. | 3% |

Example 2

Production of GGDP synthase

A polymerase chain reaction (PCR) was carried out using the above-mentioned plasmid pGGPS1 as a template, the following primers:

GGPP-I BamHI (26 mer. 5'-CGC CGA TCC ATG AGT TAC TTT GAC AA-3' (SEQ ID NO: 2), and GGPP-T EcoRI (25 mer. 5'-GG GAA TTC TTA TTT TCT CCT TCT TA-3') (SEQ ID NO: 3), and the reaction composition shown in Table 4, to amplify a DNA fragment corresponding to the coding region of GGDP synthase gene of the present invention.

TABLE 4

Reaction composition of PCR

| | |
| --- | --- |
| Template DNA | 1.0 μl |
| 10 pmol/μl primer 1 (GGPS-I BamHI) | 1.0 μl |
| 10 pmol/μl primer 2 (GGPS-T EcORI) | 1.0 μl |
| dNTP mix (Takara Shuzo) | 4.0 μl |
| AmpliTaq (5 U/μl) | 1.0 μl |
| 10x ApmliTaq buffer (Takara Shuzo) | 10.0 μl |
| 1 u/μl perfect match polymerase enhancer (Stratagene) | 1.0 μl |
| Distilled water | 81.0 μl |
| Total | 100.0 μl |

The PCR condition was 30 cycles of 90° C. for 30 seconds, 50° C. for 30 seconds and 72° C. for one minute. After finishing the reaction, the amplified DNA was precipitated with ethanol at −80° C., cleaved with a restriction enzyme EcoRI, blunt-ended, and further cleaved with a restriction enzyme BamHI to obtain a DNA fragment of about 1 kbp coding for GGDP synthase.

A commercially available plasmid pMAL-c2 (NEB, USA) was used as a cloning expression vector. In this plasmid, a DNA fragment (the name of gene: malE) coding for maltose-binding protein (sometimes designated MBP hereinafter) is inserted downstream of tac promoter, and a cloning sites for desired gene (DNA) is present downstream of the malE. Accordingly, where a gene encoding a desired polypeptide is inserted into the cloning site and the gene is expressed, then a fusion protein of the MBP and the desired polypeptide is formed, and the fusion protein can be purified in a single step by an amylose resin affinity chromatography.

The plasmid pMAL-c2 was cleaved with a restriction enzyme HindIII, blunt-ended and cleaved with a restriction enzyme BamHI. The resulting DNA fragment was ligated with the PCR-amplified DNA fragment coding for the GGDP synthase so as to obtain a recombinant plasmid pMalcGG1. The ligation and blunt-ending were carried out using a ligation kit and blunting kit of Takara Shuzo.

This recombinant plasmid was used to transform *E. coli* TOPP cell NO. 2 (Stratagene) (competent cell). The transformed cells were cultured on a YT plate medium resulting in formation of 6 colonies. These colonies were cultured in 2×YT liquid medium at 37° C., and plasmid DNA was prepared. We tested to confirm that the recombinant plasmid was correctly constructed by cleavage with EcoRV, and checking size of DNA bands by electrophoresis. Note that the correct recombinant plasmid, when cleaved with EcoRV, provides two DNA fragments of 5.1 kbp and 2.5 kbp.

The plasmid pMalcGG1 was used to transform *E. coli* pACYC-IB/DH5α (Ohnuma et al., J. Biol. Chem. 1994; 269 (20): 4792–4797) to obtain a transformant pMalcGG1, pACYC-IB/DH5α. Note, the *E. coli* pACYC-IB/DH5α already has plasmid pACYC-IB, and the pACYC-IB contains enzymes which joins two geranylgeranyl diphosphate (GGDP) (the number of carbon atoms: 20) to form phytoene, and further contains gene for desaturation, and expresses these genes.

The transformant was cultured over night in 100 ml of LB medium, and then was inoculated to 1L of LB medium, and cultured at 37° C. under the stirring conditions at 300 rpm.

Figure 4:
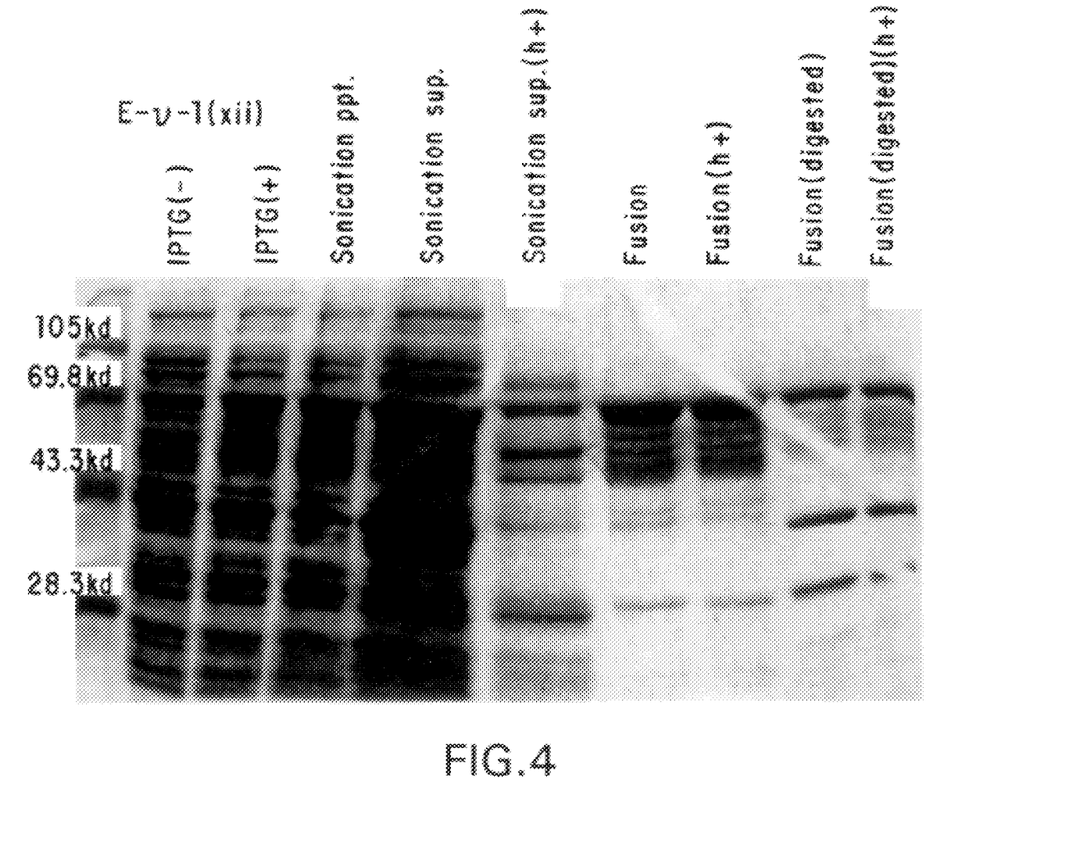
FIG. 4 represents the purification steps of the present GGDP as a fusion protein with MBP.

When cell concentration reached to kelett=30 to 40, 10 ml of 100 mM IPTG was added to the culture to induce the transcription, and culturing was further carried out for 4 hours. As a control, a sample was taken immediately before the addition of IPTG. The culture was centrifuged to collect the cells, which were then disrupted by sonication. White protein samples after induction of expression with IPTG and before induction of expression with IPTG were analyzed by SDS-polyacrylamide gel electrophoresis (SDS-page) as shown in FIG. 4 wherein IPTG (+) and IPTG (−) were referred to respectively. As a result, it was confirmed that fusion protein of about 70 kb was abundantly present in the IPTG (+) lane. SDS-page was performed according to Wiley et al., Current Protocols in Molecular Biology and using a miniproteo-II cell apparatus of Bio Rad, and gel was stained with Coomassie Brilliant Blue and dried using a gel drying kit of Promega.

The above-mentioned cell disruptant was centrifuged to fractionate into a supernatant and a precipitation. An analysis by SDS-PAGE for these fractions are shown in FIG. 4 as "Sonication sup." and "Sonication ppt." respectively. It is could be found that the fusion protein of about 70 kb was transferred to the supernatant. The supernatant was heated at 60° C. for one hour, and denatured protein was removed by centrifugation so as to obtain a supernatant. A result of analysis therefor is shown in FIG. 4 as "Sonication sup. (h+)". It is confirmed that impurity was removed and the fusion protein was enriched.

Next, the fusion protein was purified by affinity chromatography. For the purification, the above-mentioned supernatant was filtered through a 0.45 μm or 0.20 μm membrane filter, and the filtrate was passed through a column (2.5×10 cm) filled with 15 ml of amylose resin, and elution was carried out according to a protocol of NEB attached to the plasmid pMAL-c2. The eluant was desalted with PD-10 column (Pharmacia), to obtain about 3.4 mg of fusion protein. The fusion protein was heated at 60° C. for one hour. A result of SDS-PAGE for the fusion proteins prior heating and after heating is shown us "Fusion" and "Fusion (h+)" respectively. It is confirmed that the fusion protein was not denatured by heating.

Next, the fusion protein thus obtained was cleaved with Factor Xa to liberate GGDP synthase. A result of SDS-PAGE for the cleavage product is shown in FIG. 4 as "Fusion (digested)", and for the cleavage product heated at 60° C. for one hour as "Fusion (digested) (h+)". As a result, it was confirmed that GGDP synthase was partially liberated.

Figure 5:
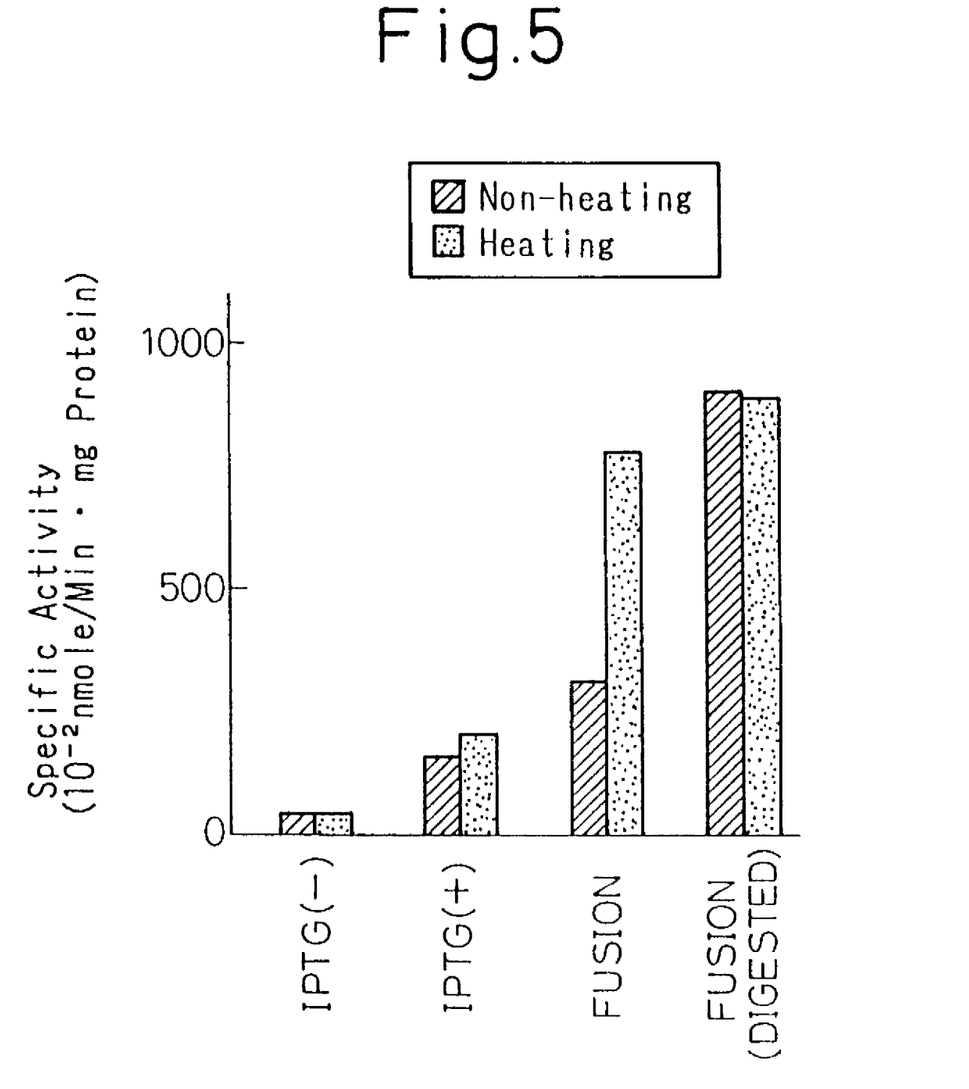
FIG. 5 is a graph showing GGDP synthase activity at each step shown in FIG. 4.

In addition, for each fraction described above, GGDP synthase activity was measured by method described in Example 1. e). This assay was carried out as follow. A solution containing 2 μg of protein, 5 mM $MgCl_2$, 10 mM $KH_2PO_4$/KOH (pH5.8), 25 μM substrate (geranye diphosphate, (all-E)-farnesyl diphosphate, or (2Z, 6E)-furnesyl diphosphate), and 463 nM $[^{14}C]$-isopentenyl diphosphate (4 Ci/mole)/ml was reacted at 55° C. for one hour, and the reaction mixture was extracted with 3 ml water-saturated butanol. One ml of the extract was used for assay of radioactivity, and the remaining portion was hydrolyzed with potato acid phosphatase, extracted, and analyzed by TLC. A result is shown in FIG. 5.

Plasmid pMalcGG1 was used to transform *E. coli* JM105 so as to obtain a transformant pMalcGG1/JM105. The transformant was cultured in TYGPN medium (20 g trypton, 10 g yeast extract, 10 ml 80% glycerol, 5 g $Na_2HPO_4$, 10 g $KNO_3$/L) for 4 hours (klett=32), induced the expression by IPTG, and further cultured for 26 hours. MBP-GGDP synthase fusion protein was purified as described above so as to obtain 21.8 mg of purified fusion protein per 1 L. Note, the broth in which the MBP-GGDP synthase fusion protein was produced was red to deep red color, and this recombinant cell was redish brown in comparison with broth and cell in which MBP alone was expressed (pMAL-c2/JM109).

Figure 6:
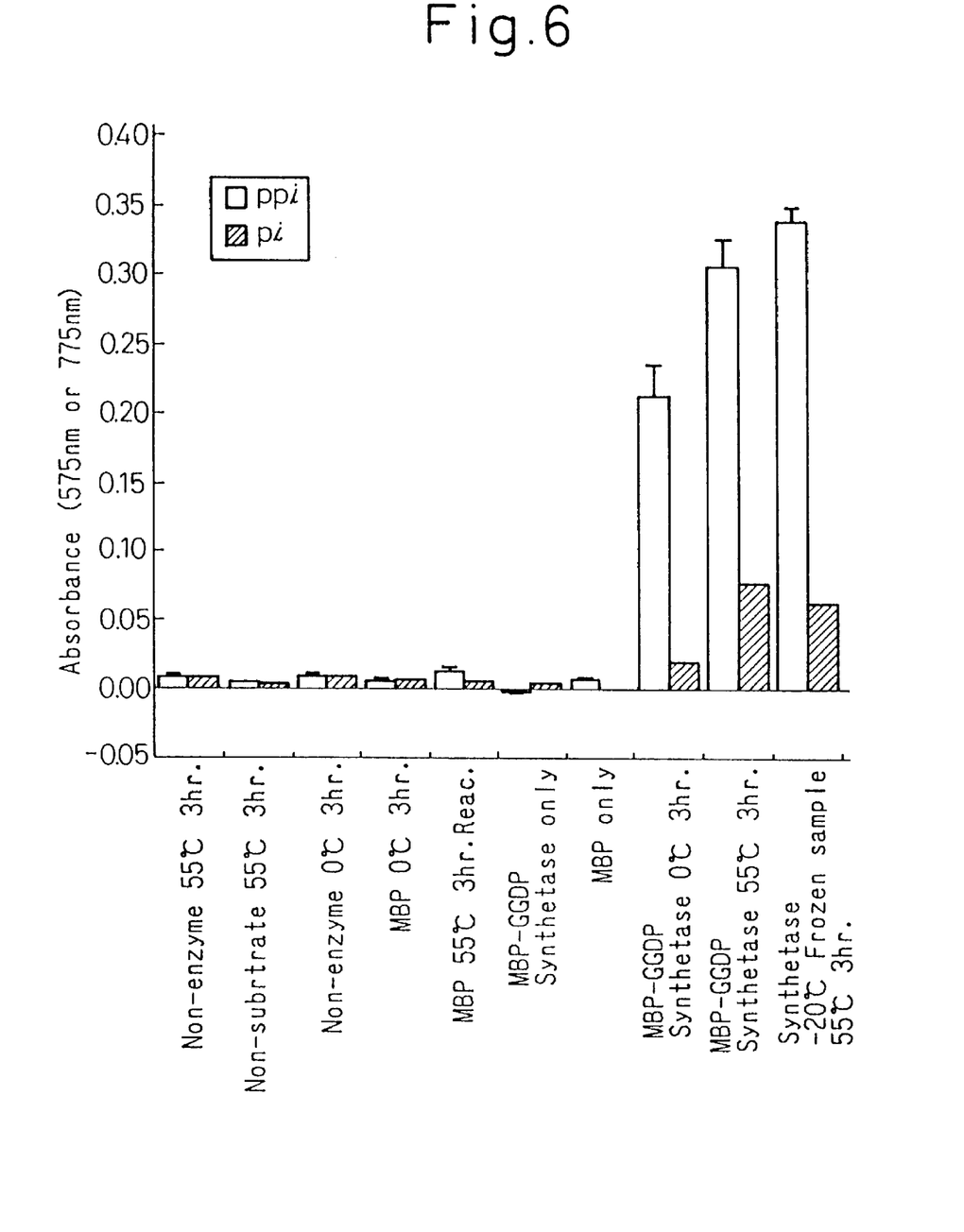
FIG. 6 is a graph showing an enzymatic activity of a purified MBP-GGDP synthase determined by Grindey-Nichol method.

GGDP synthase activity of the MBP-GGDP synthase fusion protein could be also determined by measuring inorganic phosphate according to Grindey-Nichol method (Grindy & Nichol, Anal. Biochem. 1970, 33, 114–119). A reaction mixture containing 50 mM Tris.HCl, 5 mM $MgCl_2$, 50 mM $NH_4Cl$, 10 mM 2-mercaptoethanol, 50 nmole farnesyl diphosphate, 50 nmole isopentenyl diphosphate, and for example 200 μg enzyme sample to be tested was reacted at 55° C. for 3 hours, and cooled to 0° C. to stop the reaction. Protein in the reaction mixture was denatured with trichloroacetic acid and removed, and the supernatant was neutralized with NaOH, and amounts of orthophosphate and pyrophosphate in the reaction mixture were measured to determine enzyme activity. A result is shown in FIG. 6.

Note that when GGDP synthase coding region in the expression plasmid pMalcGG1 was sequenced, the 720th nucleotide "A" was substituted by "G", and the 740th nucleotide "A" was changed to "G", resulting in change of the 247th amino acid Lys to Arg. It is assumed that the changes occurred during the PCR.

In addition, when the same experiment as described above was repeated using pGEX-2T (Pharmacia) in place of pMAL-c2, in the resulting plasmid pGluTGG1, the 823th nucleotide "A" was changed to "G", resulting in change of the 275th amino acid Met to Val. As a result, a glutathione S-transferase GGDP synthase fusion protein having a point mutation at the 275th position was obtained. This fusion protein derived from pGluTGG1 exhibited the enzyme activity as the same enzyme derived from pMalcGG1.

On the other hand, where pGEX-3X (Pharmacia) was used in place of pMAL-c2 as an expression cloning plasmid, in the resulting pGluXGG1, no mutation occurred, and glutathione S-transferase GGDP synthase fusion protein having the amino acid sequence shown in SEQ ID NO: 1 was obtained. This pGluXGG1-derived fusion protein also exhibited the same enzyme activity as the pMalcGG1-derived fused protein.

Example 3

Production of geranylgeranyl compound

Figure 7:
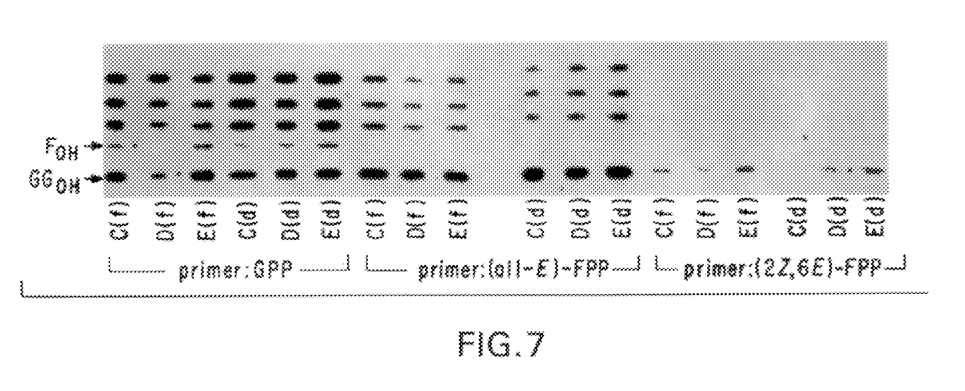
FIG. 7 is an autoradiogram of TLC showing products formed by reaction of the present fusion protein with various alyllic substrates.

Fusion proteins which were expression products of the above-mentioned expression products pMalcGG1, pGluTGG1 and pGluXGG1 as well as cleavage products (digestion products) thereof were reacted with substrates (primers), i.e., geranyldiphosphate (GPP), (all-E) farnesyl-diphosphate ([All-E]-FPP), and (2Z, 6E) furnesyl diphosphate ([2Z, 6E]-FPP). Resulting products are shown in FIG. 7.

In this figure, "C" represents a protein derived from pGluTGG1, "D" represents a protein derived from pGluXGG1, and "E" represents a protein derived from pMalcGG1. "(f)" represents a fused protein purified with an affinity column, and "(d)" represents a reaction product affinity-purified and treated with thrombin for pGluTGG1, and a product affinity-purified and treated with Factor-Xa for pGluXGG1 and pMalcGG1.

According to the present invention, DNA sequence coding for GGDP synthase derived from *Sulfolobus acidocaldarius* is provided. Recombinant cells, such as *E. coli* cells, transformed with an expression plasmid containing said DNA fragment produce stable, especially thermostable enzyme having geranylgeranyl diphosphate activity and geranylgeranyl diphosphate.

---

We claim:

1. An isolated DNA comprising a nucleotide sequence encoding geranylgeranyl diphosphate synthase of *Sulfolobus acidocaldarius*.

2. The DNA according to claim 1, wherein the nucleotide sequence encodes an amino acid sequence of SEQ ID NO: 4.

3. DNA according to claim 1, wherein the nucleotide sequence comprises SEQ ID NO: 1.

4. An isolated DNA comprising a nucleotide sequence encoding a modified geranylgeranyl diphosphate synthase derived from a geranylgeranyl diphosphate synthase endogenous to *Sulfolobus acidocaldarius* and comprising one or more insertions, deletions or substitutions of a codon from a non-essential region of said endogenous geranylgeranyl diphosphate synthase, wherein said modified geranylgeranyl diphosphate synthase has the enzymatic activity of a geranylgeranyl diphosphate synthase endogenous to *S. acidocaldarius*.

5. The DNA of claim 4 wherein the nucleotide sequence encodes a modified geranylgeranyl diphosphate synthase comprising an amino acid sequence having at least 90% identity to SEQ ID NO: 4.

6. The DNA of claim 4 wherein the nucleotide sequence encodes a modified geranylgeranyl diphosphate synthase comprising an amino acid sequence having at least 95% identity to SEQ ID NO: 4.

7. The DNA of claim 4 wherein the nucleotide sequence encodes a modified geranylgeranyl diphosphate synthase having an amino acid sequence that differs from the amino acid sequence in SEQ ID NO: 4 at position 247 or 275 or at both positions 247 and 275.

8. A recombinant vector comprising DNA according to claim 1 and an additional nucleotide sequence for regulating the expression of said DNA.

9. A recombinant vector comprising DNA according to claim 1 wherein the DNA further comprises a nucleotide sequence encoding a fusion partner and an additional nucleotide sequence for regulating the expression of said DNA.

10. A recombinant vector comprising DNA according to claim 9 wherein the fusion partner is selected from the group consisting of a maltose binding protein and a glutathione-S-transferase protein.

11. A recombinant microbial cell which is transformed with a recombinant vector according to claim 8.

12. A recombinant microbial cell according to claim 11, wherein the host belongs to the genus *Escherichia*.

13. A recombinant microbial cell which is transformed with a recombinant vector according to claim 9.

14. A recombinant microbial cell which is transformed with a recombinant vector according to claim 10.

15. A process for production of geranylgeranyl diphosphate synthase comprising the steps of culturing the recombinant microbial cell according to claim 11 in a medium, and recovering geranylgeranyl diphosphate synthase.

16. A process for production of geranylgeranyl diphosphate synthase comprising the steps of culturing the recombinant microbial cell according to claim 13 in a medium, and recovering a geranylgeranyl diphosphate synthase fusion protein encoding a enzymatically active geranylgeranyl diphosphate synthase.

17. A process for production of geranylgeranyl diphosphate synthase comprising the steps of culturing the recombinant microbial cell according to claim 13 in a medium, obtaining a geranylgeranyl diphosphate synthase fusion protein, and liberating a enzymatically active geranylgeranyl diphosphate synthase from the fusion protein.

18. A process for production of geranylgeranyl diphosphate synthase comprising the steps of culturing the recombinant microbial cell according to claim 14 in a medium, and recovering a geranylgeranyl diphosphate synthase fusion protein encoding a enzymatically active geranylgeranyl diphosphate synthase.

19. A process for production of geranylgeranyl diphosphate comprising reacting a culture of the recombinant microbial cell according to claim 11 or geranylgeranyl diphosphate synthase isolated from said culture with a substrate selected from the group consisting of isopentyl diphosphate, dimethylallyl diphosphate, geranyl diphosphate and farnesyl diphosphate.

20. A process for the production of geranylgeranyl diphosphate comprising reacting a geranylgeranyl diphosphate synthase fusion protein obtained by a process according to claim 16 with a substrate selected from the group consisting of isopentyl diphosphate, dimethylallyl diphosphate, geranyl diphosphate and farnesyl diphosphate.

21. A process for production of geranylgeranyl diphosphate comprising reacting a culture of the recombinant microbial cell according to claim 14 or a geranylgeranyl diphosphate synthase fusion protein isolated from said culture with a substrate selected from the group comprising isopentyl diphosphate, dimethylallyl diphosphate, geranyl diphosphate and farnesyl diphosphate.

* * * * *

UNITED STATES PATENT AND TRADEMARK OFFICE
CERTIFICATE OF CORRECTION

PATENT NO. : 5,773,273
DATED : June 30, 1998
INVENTOR(S) : Tokuzo NISHINO, et al.

It is certified that error appears in the above-identified patent and that said Letters Patent is hereby corrected as shown below:

Column 6, line 36, change "550 C." to --55 C.--.

Column 8, line 30, change "...EcORI)" to --...EcoRI)--.

Column 17, line 8, insert --The-- before "DNA".

Signed and Sealed this

Third Day of April, 2001

Attest:

NICHOLAS P. GODICI

*Attesting Officer*  *Acting Director of the United States Patent and Trademark Office*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 990 base pairs
        ( B ) TYPE: nucleic acid
        ( C ) STRANDEDNESS: double
        ( D ) TOPOLOGY: linear     ( i i ) MOLECULE TYPE: DNA (genomic)

( i i i ) HYPOTHETICAL: NO

( v i ) ORIGINAL SOURCE:
        ( A ) ORGANISM: Sulfolobus acidocaldarius
        ( B ) STRAIN: ATCC 33909

( i x ) FEATURE:
        ( A ) NAME/KEY: CDS
        ( B ) LOCATION: 1-990

( x i ) SEQUENCE DESCRIPTION: SEQ ID NO:1:

```
ATG  AGT  TAC  TTT  GAC  AAC  TAT  TTT  AAT  GAG  ATT  GTT  AAT  TCT  GTA  AAC      48
Met  Ser  Tyr  Phe  Asp  Asn  Tyr  Phe  Asn  Glu  Ile  Val  Asn  Ser  Val  Asn
                         5                    10                        15

GAC  ATT  ATT  AAG  AGC  TAT  ATA  TCT  GGA  GAT  GTT  CCT  AAA  CTA  TAT  GAA      96
Asp  Ile  Ile  Lys  Ser  Tyr  Ile  Ser  Gly  Asp  Val  Pro  Lys  Leu  Tyr  Glu
                    20                   25                        30

GCC  TCA  TAT  CAT  TTG  TTT  ACA  TCT  GGA  GGT  AAG  AGG  TTA  AGA  CCA  TTA     144
Ala  Ser  Tyr  His  Leu  Phe  Thr  Ser  Gly  Gly  Lys  Arg  Leu  Arg  Pro  Leu
               35                        40                    45

ATC  TTA  ACT  ATA  TCA  TCA  GAT  TTA  TTC  GGA  GGA  CAG  AGA  GAA  AGA  GCT     192
Ile  Leu  Thr  Ile  Ser  Ser  Asp  Leu  Phe  Gly  Gly  Gln  Arg  Glu  Arg  Ala
          50                        55                    60

TAT  TAT  GCA  GGT  GCA  GCT  ATT  GAA  GTT  CTT  CAT  ACT  TTT  ACG  CTT  GTG     240
Tyr  Tyr  Ala  Gly  Ala  Ala  Ile  Glu  Val  Leu  His  Thr  Phe  Thr  Leu  Val
 65                        70                        75                    80

CAT  GAT  GAT  ATT  ATG  GAT  CAA  GAT  AAT  ATC  AGA  AGA  GGG  TTA  CCC  ACA     288
His  Asp  Asp  Ile  Met  Asp  Gln  Asp  Asn  Ile  Arg  Arg  Gly  Leu  Pro  Thr
                         85                        90                    95

GTC  CAC  GTG  AAA  TAC  GGC  TTA  CCC  TTA  GCA  ATA  TTA  GCT  GGG  GAT  TTA     336
Val  His  Val  Lys  Tyr  Gly  Leu  Pro  Leu  Ala  Ile  Leu  Ala  Gly  Asp  Leu
                   100                       105                       110

CTA  CAT  GCA  AAG  GCT  TTT  CAG  CTC  TTA  ACC  CAG  GCT  CTT  AGA  GGT  TTG     384
Leu  His  Ala  Lys  Ala  Phe  Gln  Leu  Leu  Thr  Gln  Ala  Leu  Arg  Gly  Leu
              115                       120                       125

CCA  AGT  GAA  ACC  ATA  ATT  AAG  GCT  TTC  GAT  ATT  TTC  ACT  CGT  TCA  ATA     432
Pro  Ser  Glu  Thr  Ile  Ile  Lys  Ala  Phe  Asp  Ile  Phe  Thr  Arg  Ser  Ile
         130                       135                       140

ATA  ATT  ATA  TCC  GAA  GGA  CAG  GCA  GTA  GAT  ATG  GAA  TTT  GAG  GAC  AGA     480
Ile  Ile  Ile  Ser  Glu  Gly  Gln  Ala  Val  Asp  Met  Glu  Phe  Glu  Asp  Arg
145                      150                       155                      160
```

| | | | | | | | | | | | | | | | |
|---|---|---|---|---|---|---|---|---|---|---|---|---|---|---|---|
| ATT | GAT | ATA | AAG | GAG | CAG | GAA | TAC | CTT | GAC | ATG | ATC | TCA | CGT | AAG | ACA | 528
| Ile | Asp | Ile | Lys | Glu | Gln | Glu | Tyr | Leu | Asp | Met | Ile | Ser | Arg | Lys | Thr |
| | | | 165 | | | | | 170 | | | | | | 175 | |
| GCT | GCA | TTA | TTC | TCG | GCA | TCC | TCA | AGT | ATA | GGC | GCA | CTT | ATT | GCT | GGT | 576
| Ala | Ala | Leu | Phe | Ser | Ala | Ser | Ser | Ser | Ile | Gly | Ala | Leu | Ile | Ala | Gly |
| | | | 180 | | | | | 185 | | | | | 190 | | |
| GCT | AAT | GAT | AAT | GAT | GTA | AGA | CTG | ATG | TCT | GAT | TTC | GGT | ACG | AAT | CTA | 624
| Ala | Asn | Asp | Asn | Asp | Val | Arg | Leu | Met | Ser | Asp | Phe | Gly | Thr | Asn | Leu |
| | | 195 | | | | | 200 | | | | | 205 | | | |
| GGT | ATT | GCA | TTT | CAG | ATT | GTT | GAC | GAT | ATC | TTA | GGT | CTA | ACA | GCA | GAC | 672
| Gly | Ile | Ala | Phe | Gln | Ile | Val | Asp | Asp | Ile | Leu | Gly | Leu | Thr | Ala | Asp |
| | 210 | | | | | 215 | | | | | 220 | | | | |
| GAA | AAG | GAA | CTT | GGA | AAG | CCT | GTT | TTT | AGT | GAT | ATT | AGG | GAG | GGT | AAA | 720
| Glu | Lys | Glu | Leu | Gly | Lys | Pro | Val | Phe | Ser | Asp | Ile | Arg | Glu | Gly | Lys |
| 225 | | | | | 230 | | | | | 235 | | | | | 240 |
| AAG | ACT | ATA | CTT | GTA | ATA | AAA | ACA | CTG | GAG | CTT | TGT | AAA | GAG | GAC | GAG | 768
| Lys | Thr | Ile | Leu | Val | Ile | Lys | Thr | Leu | Glu | Leu | Cys | Lys | Glu | Asp | Glu |
| | | | | 245 | | | | | 250 | | | | | 255 | |
| AAG | AAG | ATT | GTC | CTA | AAG | GCG | TTA | GGT | AAT | AAG | TCA | GCC | TCA | AAA | GAA | 816
| Lys | Lys | Ile | Val | Leu | Lys | Ala | Leu | Gly | Asn | Lys | Ser | Ala | Ser | Lys | Glu |
| | | | 260 | | | | | 265 | | | | | 270 | | |
| GAA | TTA | ATG | AGC | TCA | GCA | GAT | ATA | ATT | AAG | AAA | TAC | TCT | TTA | GAT | TAT | 864
| Glu | Leu | Met | Ser | Ser | Ala | Asp | Ile | Ile | Lys | Lys | Tyr | Ser | Leu | Asp | Tyr |
| | | 275 | | | | | 280 | | | | | 285 | | | |
| GCA | TAC | AAT | TTA | GCA | GAG | AAA | TAT | TAT | AAA | AAT | GCT | ATA | GAC | TCT | TTA | 912
| Ala | Tyr | Asn | Leu | Ala | Glu | Lys | Tyr | Tyr | Lys | Asn | Ala | Ile | Asp | Ser | Leu |
| | 290 | | | | | 295 | | | | | 300 | | | | |
| AAT | CAA | GTC | TCC | TCT | AAG | AGT | GAT | ATA | CCT | GGA | AAG | GCT | TTA | AAA | TAT | 960
| Asn | Gln | Val | Ser | Ser | Lys | Ser | Asp | Ile | Pro | Gly | Lys | Ala | Leu | Lys | Tyr |
| 305 | | | | | 310 | | | | | 315 | | | | | 320 |
| CTA | GCT | GAA | TTT | ACG | ATA | AGA | AGG | AGA | AAA | | | | | | | 990
| Leu | Ala | Glu | Phe | Thr | Ile | Arg | Arg | Arg | Lys | | | | | | |
| | | | | 325 | | | | 330 | | | | | | | |

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( x i ) SEQUENCE DESCRIPTION: SEQ ID NO:2:

CGCGGATCCA TGAGTTACTT TGACAA    26

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( x i ) SEQUENCE DESCRIPTION: SEQ ID NO:3:

GGGAATTCTT ATTTTCTCCT TCTTA    25

( 2 ) INFORMATION FOR SEQ ID NO:4:

( i ) SEQUENCE CHARACTERISTICS:
        ( A ) LENGTH:330 amino acids
        ( B ) TYPE: amino acid
        ( D ) TOPOLOGY: linear     ( i i ) MOLECULE TYPE: protein     ( i i i ) HYPOTHETICAL: NO     ( v i ) ORIGINAL SOURCE:
        ( A ) ORGANISM: Sulfolobus acidocaldarius
        ( B ) STRAIN: ATCC 33909

( x i ) SEQUENCE DESCRIPTION: SEQ ID NO:4:

```
Met  Ser  Tyr  Phe  Asp  Asn  Tyr  Phe  Asn  Glu  Ile  Val  Asn  Ser  Val  Asn
                    5                        10                      15

Asp  Ile  Ile  Lys  Ser  Tyr  Ile  Ser  Gly  Asp  Val  Pro  Lys  Leu  Tyr  Glu
               20                        25                      30

Ala  Ser  Tyr  His  Leu  Phe  Thr  Ser  Gly  Gly  Lys  Arg  Leu  Arg  Pro  Leu
          35                        40                      45

Ile  Leu  Thr  Ile  Ser  Ser  Asp  Leu  Phe  Gly  Gly  Gln  Arg  Glu  Arg  Ala
     50                        55                      60

Tyr  Tyr  Ala  Gly  Ala  Ala  Ile  Glu  Val  Leu  His  Thr  Phe  Thr  Leu  Val
65                       70                       75                            80

His  Asp  Asp  Ile  Met  Asp  Gln  Asp  Asn  Ile  Arg  Arg  Gly  Leu  Pro  Thr
                    85                        90                      95

Val  His  Val  Lys  Tyr  Gly  Leu  Pro  Leu  Ala  Ile  Leu  Ala  Gly  Asp  Leu
               100                       105                     110

Leu  His  Ala  Lys  Ala  Phe  Gln  Leu  Leu  Thr  Gln  Ala  Leu  Arg  Gly  Leu
          115                       120                     125

Pro  Ser  Glu  Thr  Ile  Ile  Lys  Ala  Phe  Asp  Ile  Phe  Thr  Arg  Ser  Ile
     130                       135                     140

Ile  Ile  Ile  Ser  Glu  Gly  Gln  Ala  Val  Asp  Met  Glu  Phe  Glu  Asp  Arg
145                      150                      155                          160

Ile  Asp  Ile  Lys  Glu  Gln  Glu  Tyr  Leu  Asp  Met  Ile  Ser  Arg  Lys  Thr
                    165                       170                     175

Ala  Ala  Leu  Phe  Ser  Ala  Ser  Ser  Ile  Gly  Ala  Leu  Ile  Ala  Gly
               180                       185                     190

Ala  Asn  Asp  Asn  Asp  Val  Arg  Leu  Met  Ser  Asp  Phe  Gly  Thr  Asn  Leu
          195                       200                     205

Gly  Ile  Ala  Phe  Gln  Ile  Val  Asp  Asp  Ile  Leu  Gly  Leu  Thr  Ala  Asp
     210                       215                     220

Glu  Lys  Glu  Leu  Gly  Lys  Pro  Val  Phe  Ser  Asp  Ile  Arg  Glu  Gly  Lys
225                      230                      235                          240

Lys  Thr  Ile  Leu  Val  Ile  Lys  Thr  Leu  Glu  Leu  Cys  Lys  Glu  Asp  Glu
                    245                       250                     255

Lys  Lys  Ile  Val  Leu  Lys  Ala  Leu  Gly  Asn  Lys  Ser  Ala  Ser  Lys  Glu
               260                       265                     270

Glu  Leu  Met  Ser  Ser  Ala  Asp  Ile  Ile  Lys  Lys  Tyr  Ser  Leu  Asp  Tyr
          275                       280                     285

Ala  Tyr  Asn  Leu  Ala  Glu  Lys  Tyr  Tyr  Lys  Asn  Ala  Ile  Asp  Ser  Leu
     290                       295                     300

Asn  Gln  Val  Ser  Ser  Lys  Ser  Asp  Ile  Pro  Gly  Lys  Ala  Leu  Lys  Tyr
305                      310                      315                          320

Leu  Ala  Glu  Phe  Thr  Ile  Arg  Arg  Arg  Lys
                    325                       330
```